US008405832B2

(12) United States Patent
Schmaelzle et al.

(10) Patent No.: US 8,405,832 B2
(45) Date of Patent: Mar. 26, 2013

(54) LIGHT SCATTERING MEASUREMENT SYSTEM BASED ON FLEXIBLE SENSOR ARRAY

(75) Inventors: Philipp Helmut Schmaelzle, Los Altos, CA (US); Robert A. Street, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 559 days.

(21) Appl. No.: 12/635,369

(22) Filed: Dec. 10, 2009

(65) Prior Publication Data

US 2011/0141476 A1    Jun. 16, 2011

(51) Int. Cl.
 *G01J 1/00* (2006.01)
 *G01J 3/00* (2006.01)
 *G01N 21/55* (2006.01)
(52) U.S. Cl. .......... 356/445; 356/213; 356/300
(58) Field of Classification Search .......... 356/445–448, 356/450–458
See application file for complete search history.

(56) References Cited

U.S. PATENT DOCUMENTS

| | | | | |
|---|---|---|---|---|
| 4,218,144 A * | 8/1980 | Whitehouse et al. | ......... | 356/446 |
| 5,196,906 A | 3/1993 | Stover | | |
| 6,034,776 A * | 3/2000 | Germer et al. | ......... | 356/369 |
| 7,433,031 B2 * | 10/2008 | Xu et al. | ......... | 356/237.2 |
| 7,619,754 B2 * | 11/2009 | Riel et al. | ......... | 356/625 |
| 7,929,142 B2 * | 4/2011 | Ben-Ezra et al. | ......... | 356/445 |
| 8,077,235 B2 * | 12/2011 | Street | ......... | 348/294 |
| 2008/0068593 A1 * | 3/2008 | Nakano et al. | ......... | 356/73 |
| 2008/0151084 A1 * | 6/2008 | Lu et al. | ......... | 348/294 |
| 2008/0151089 A1 * | 6/2008 | Street et al. | ......... | 348/308 |
| 2009/0184954 A1 | 7/2009 | Street | | |

OTHER PUBLICATIONS

Codixx web page on patterned polarizing filters: http://web.archive.org/web/20070203080620/http://www.codixx.de/cms/polarizers/polarizer/patterned-structured.html.*

* cited by examiner

*Primary Examiner* — Gregory J Toatley
*Assistant Examiner* — Jarreas C Underwood
(74) *Attorney, Agent, or Firm* — Marger Johnson & McCollom PC

(57) ABSTRACT

A compact, optical measurement system has a non-flat detector array having multiple detector elements arranged on a flexible substrate in a monolithic fashion, one or more illumination sources arranged to provide more than one angle of incidence of light on a subject being measured, and a detection system in electrical communication with the detector array, the detection system arranged to receive inputs from the detector array and provide a measurement from the inputs. A method of measuring reflectance of a surface includes placing the surface adjacent a hemispherical detector array, illuminating the surface from a predetermined angle of incidence, simultaneously detecting reflectance at multiple emission angles using the hemispherical detector array, and repeating the illuminating and detecting processes at different angles of incidence. Optional arrays of lenses, baffles and filters may be employed by the system.

15 Claims, 3 Drawing Sheets

LIGHT SCATTERING MEASUREMENT SYSTEM BASED ON FLEXIBLE SENSOR ARRAY

BACKGROUND

The Bi-directional Reflectance Distribution Function (BRDF) of a surface area element assigns transfer coefficients to each pair of incident angles and reflected/scattered angles. These coefficients translate from incoming irradiance/illuminance to outgoing radiance/luminance and take the form of a ratio. When sampling a point like region over extended solid angles, the obtained BRDF is a function of 4 scalars denoting angles and characterizes a fundamental optical property of the surface at this location. The result is dependent on polarization, wavelength, coherence, etc. of the probing light and may differ for different positions on a surface. It can be appreciated that the high dimensional signature conveyed by a BRDF may serve as proxy for material properties, the relevance of which extends well beyond the field of optics. Many fields employ BRDF measurements, or subsets of it, for applications including medical diagnostics, anti-counterfeiting, gloss evaluation, printing media recognition, optical design and computer graphics.

Materials can have unique values of these properties and one may build a library of known materials and their properties. When an unknown sample is encountered, the BRDF measurement results may indicate the type of material. Known materials may also undergo measurement to determine the properties of the surface and from those properties may convey information about architecture, general product design, paint development, topography, materials fabrication, print quality, coatings and other situation when the appearance of a surface is important.

Typically, the BRDF measurement requires the measurement of the scattered light intensity from a surface and its dependence upon the incident and scattered angles, for any particular illumination wavelength. These measurements are typically done using a collimated light source and an individual detector that is moved to different scattering angles for each angle of incidence. For each angle of incidence, the number of positions of the detector, the signal integration time, the time to move the detector and the number of wavelengths combine to make the measurement rather slow. In addition, the apparatus used to make such a measurement is rather large, in part because the mechanics needed to move the detector from position to position. A more compact BRDF system is needed, as well as one that is faster and less expensive.

DETAILED DESCRIPTION OF THE EMBODIMENTS

Figure 1:
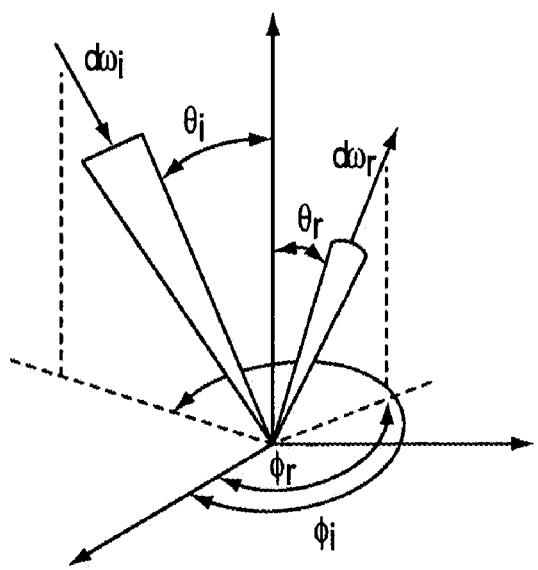
FIG. 1 shows a diagram of various parameters used in making BRDF measurements.

FIG. 1 shows a diagram of various parameters used in making BRDF measurements. In the diagram, angles designated with the subscript i indicate angles of incidence of the light, and angles designated with the subscript r indicate angles of reflectance. Using these measurements, the transfer of the BRDF from an angular spectrum of irradiance to an angular spectrum of radiance is given by:

$$f(\theta_i, \phi_i, \theta_r, \phi_r) = \frac{dL_r(\theta_r, \phi_r)}{dE_i(\theta_i, \phi_i)}.$$

Typically, this measurement is done with a collimated light source and an individual detector moved to different scattering angles for each angle of incidence. This process generally requires a large apparatus and takes a relatively long amount of time.

The BRDF measurement is in its most natural form when in polar coordinates. Therefore, the detector could assume measuring locations that are arranged on a spherical surface, or an approximation of a spherical surface. In a conventional BRDF measurement system, the number of positions for the detector (N), the number of positions for the source (M), the signal integration time $(T_I)$ the time to move the detector $(T_M)$, and the number of wavelengths (W) combine to make the measurement rather slow. The total time is $N*M*W*(T_I+T_M)$. If an integrated system could use a detector array rather than a single detector without sacrificing the beneficially wide angular coverage, all detector angles can be sampled simultaneously. This would reduce the measurement time to $1*M*W(T_I+T_M)$, a reduction by the factor N, typically a large number in the range 1,000-100,000.

Figure 2:
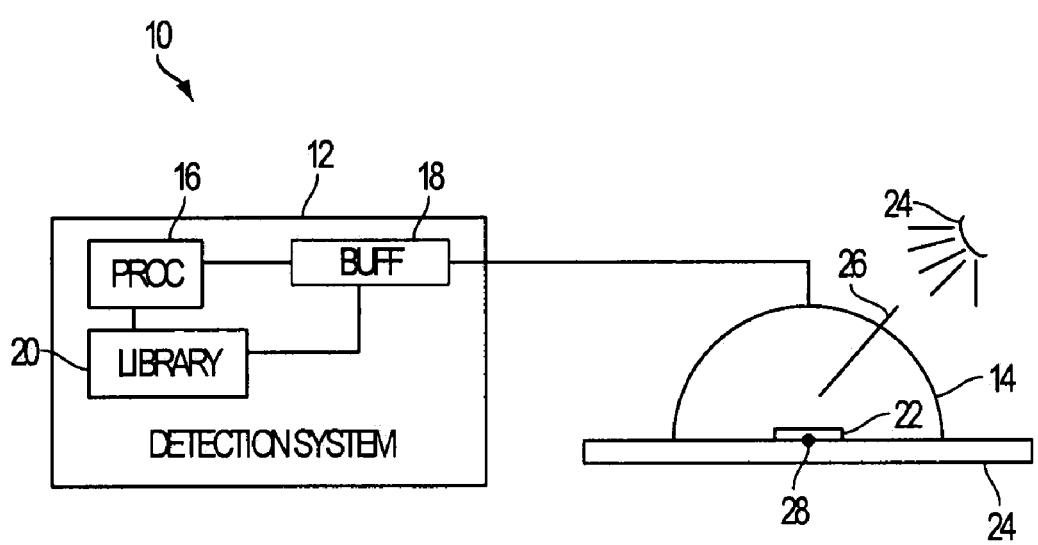
FIG. 2 shows an embodiment of a BRDF measurement system.

FIG. 2 shows an example of a BRDF measuring system 10. The measurement system 10 includes a detection system 12 and a detector 14. The detection system 12 may include a processor 16 that receives inputs from the detector 14. The reception may include buffering the incoming data in buffer 18. The processor 16 may analyze the data to analyze the material under inspection 22. Besides various data processing steps known to those skilled in the art such as Fourier transforms, peak detection, thresholding, etc., this analysis may include accessing properties of known materials, or appropriate parameters for the material under inspection, which may be stored in a library, database or other type of storage 20.

The material under inspection 22 undergoes inspection by the detector 14, in this embodiment a hemispherical detector array 14. In this embodiment, the material under inspection 22 will generally be placed at point 28 and is illuminated by the light source 24. In this particular embodiment, the illumination source 24 is external to the detector array 14. The illumination reaches the material under inspection through the slit 26.

The detector array 14 is formed in a hemispherical shape or otherwise formed into a curved or non-flat configuration. This allows multiple detectors to be arranged around the material under inspection, allowing multiple angles of incidence to be detected and recorded for each angle of illumination. This speeds the process of characterizing the material under inspection. The detector array may be formed on a flexible substrate such as plastic and consist of an active matrix array of thin film light sensors. The design may include a cut pattern, in which the elements are arranged around regions of the substrate that are subsequently cut and then the substrate bent into an approximation of a spherical shape. The thin film transistors and photodiodes may be made of amorphous silicon, organic semiconductors, or other suitable material.

Forming the detector array may be accomplished in several ways. Examples of how an electronic device having an array of elements is formed may be found in US Patent Publication No. 20090184954, and U.S. patent application Ser. No. 12/253,390. The use of detectors formed in such a manner is discussed in US Patent Publication Nos. 20080151084 and 20080151089. However, neither of these shows using a hemispherical array with the detectors on the interior curve.

Figure 3:
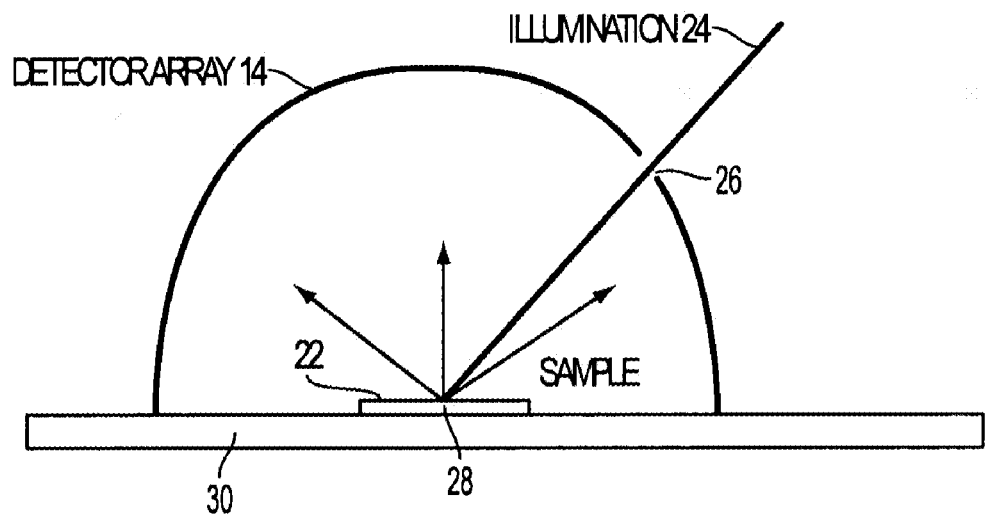
FIG. 3 shows an embodiment of a sensor array.
Figure 4:
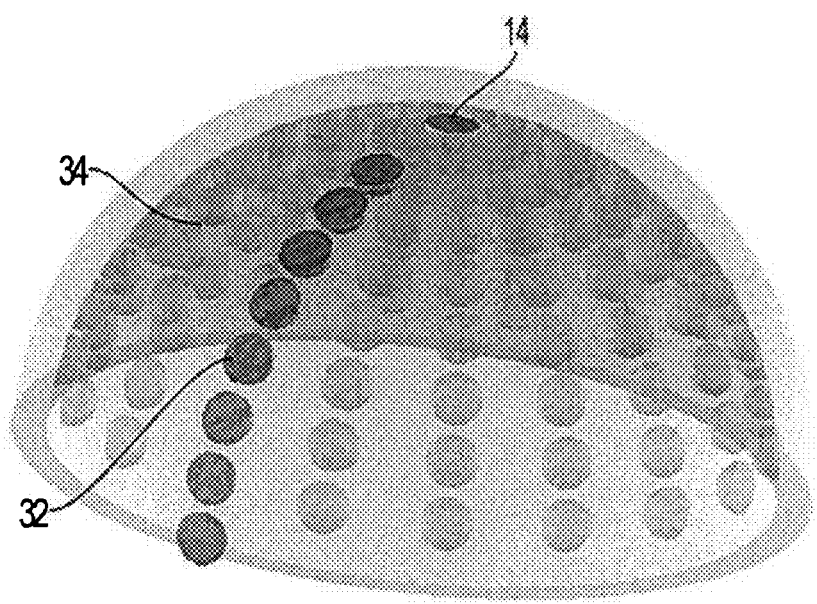
FIG. 4 shows an alternative embodiment of a sensor array.

As mentioned above, the illumination in the system 10 reaches the matter under inspection through a slit. Other options are available. FIGS. 3 and 4 show alternative embodiments of illumination for the material under inspection. In FIG. 3, the detector array 14 is arranged over the material under inspection to allow detection at multiple angles of reflection. The illumination 24 enters the detector array through the slit 26, and reaches the material under inspection 22. The material under inspection 22 may be mounted on platform 30. The slit 26 may be oriented down the side of the detector array from the vertex to the edge to allow changing of the illumination's zenith angle.

The slit from the vertex to the edge of the array allows variance of the zenith angle, theta, while the azimuth angle, phi, can be controlled mechanically, such as by rotating the entire assembly. The platform 30 may rotate around an axis normal to the surface to allow detection at multiple angles of phi. Generally, to avoid excessive background light inside the sensor half sphere, the illumination should mostly be confined to the measurement spot 28. It may be beneficial to add an absorptive plate with a small aperture between the sensor hemisphere and the material under inspection leaving open only the measurement region around 28.

In an alternative configuration, the illumination may be integrated into the detector array. FIG. 4 shows an example of this. In FIG. 4, the detector array 14 consists of an array of detectors 34 positioned on the inside of the hemisphere. The positions of the detectors allow for the processing of multiple detected angles of incidence and reflectance simultaneously. In addition to the detector elements, the array could include illumination elements such as 32, which may be light emitting diodes (LEDs) or other solid state illumination devices, such as laser diodes, LEDs, lasers, organic LEDs (OLEDs), as well as any other suitable source.

The resulting system would be much faster, simpler and more compact than current systems. In operation, the material is placed under the non-flat detector array, or the detector array is placed on a surface to be measured. Illumination is provided, either through the slit or from an interior light source or other means, as discussed above, then reading out the signals from the detector array. Each detector corresponds to a different reflection angle. The measurement is then repeated for different illumination angles of incidence and wavelengths as needed. The position of each of the detector elements is known from the design, so the reflection angle with regard to the illuminated surface is known.

The detector array 14 may be made with a wide range in the number of elements. An exemplary design may have on the order of 10,000 elements on an array in which the element size is approximately 0.5 mm, and the radius of the sphere is approximately 3 cm. The angular coverage can approach the full hemisphere. This results in an angular resolution of about 1 degree. Lower resolutions make the design and fabrication of the array less complex. Higher resolutions may be beneficial for some application, and can be achieved at moderate addition manufacturing complexity for localized zones of interest, or at elevated complexity for the entire hemisphere.

The pixel element may contain a thin film photodiode to sense the reflected light and a thin film transistor to allow the pixel to be addressed by external electronics. The photodiode and the thin film transistor may be fabricated from amorphous silicon, an organic semiconductor or other thin film semiconductor. Fabrication of the device may use photolithography or another printing technique.

For accurate BRDF measurements, a system needs to minimize stray light reflections. On the one hand, the concave shape towards the lighted volume aggravates stray light concerns, since detector elements have line of sight to other components illuminated by stray light. However, the concave shape is beneficial for the overall system design and therefore valued. On the other hand, using a spherical shape as a special case of a concave shape helps minimize stray reflections. Typically, the surface reflected light will not be oriented to impinge on other detectors. The detectors may have an antireflection coating and baffle structures, for example radial baffle structures, provided as a pre-manufactured component, such as a film, around each detector to absorb unwanted light, minimizing stray reflections.

Figure 5:
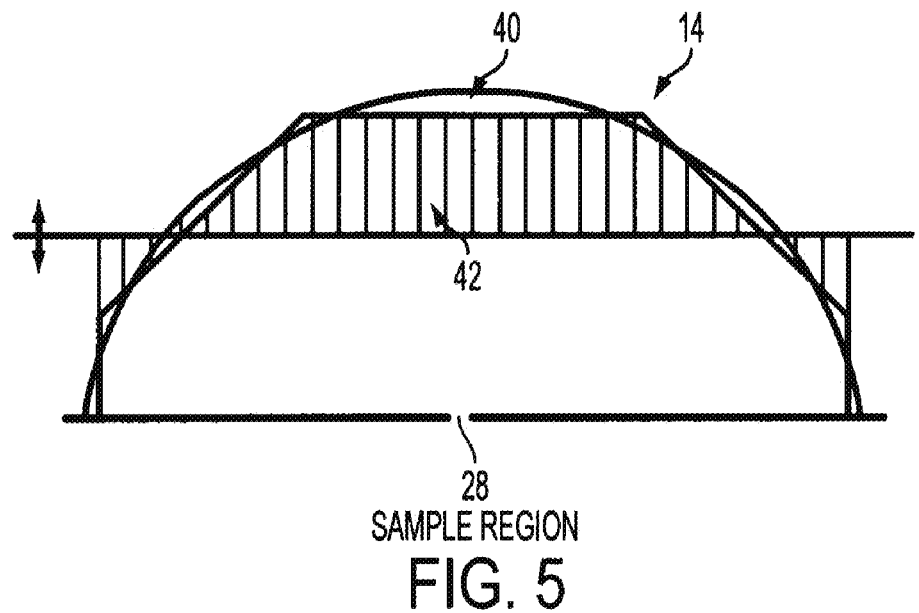
FIG. 5 shows an embodiment of a sensor array.

In addition to minimizing stray reflections, the spherical approximation of the detector array results in each detector being oriented similarly to the illuminated area. One could think of the detectors as being located in positions more closely located to a sphere than to any particular plane through the detectors. FIG. 5 shows an example detector with an imaginary plane through the detector array. The detector array 14 as shown here is an approximation of a sphere. As can be seen the detector locations at the perimeter of the approximation deviate from a sphere in the regions 40. If one were to draw a line through the detector, the deviation from the plane is shown by the region 42. As shown, then, the detector elements are arranged such that their location is closer to a sphere centered on the sample region than any chosen plane.

The availability of a compact, fast BRDF measurement system has several applications. In the medical realm, for example, skin cancer detection, blood analysis, bacterial colony typing by laser diffraction, oxidative stress of cells, and detector modality for a flow cytometer. In cosmetics, specular skin light distribution, and quantifying with/without makeup. In copying and printing application, it could be used in media recognition, such as different types of print substrates with different types of gloss, and gloss evaluation after printing, as well as advanced gloss metering. It could be used in verifying security patterns, such as diffractive patterns used in concert tickets and various types of packaging, or holograms. It could be used in surface data acquisition for photo realistic three-dimensional modeling used in video games, movies, architectural, and other types of visualization and/or appearance simulation technologies. Other applications include the use as a standardized evaluation tool for reflecting or redirecting material, as in the domains of solar energy and lighting, angular light distribution, quality assurance for scattering materials or various metrology aspects. In conjunction with a separate/exchangeable sensor part such as a stretchable diffractive grating, a SPR chip, etc., a compact BRDF sensor could also be used as a general purpose readout element. It may also be attractive to use a BRDF sensor well below its capability, if it happens to be integrated already into a system or if its cost should become commoditized by standardization and possible future mass production. To give a trivial example for the latter, a BRDF sensors output could be easily exploited to detect finger touch like a button or generally the distance of a nearby object.

Further variations and modifications are of course possible. In the particular embodiments described above, a process of manufacture was used in which the light sources were assembled onto the hemispherical detector at a late stage in the manufacturing process. The light sources were separately manufactured sub-assemblies, such as off-the-shelf laser diodes.

However, integrating the illumination elements would lead to a monolithic construction of the entire sensing part. This would be possible by interspersing the illumination elements, such as OLED elements, with the matrix of photoreceptors. This presents several challenges because of the different levels of driving currents, different materials and processing steps.

Figure 6:
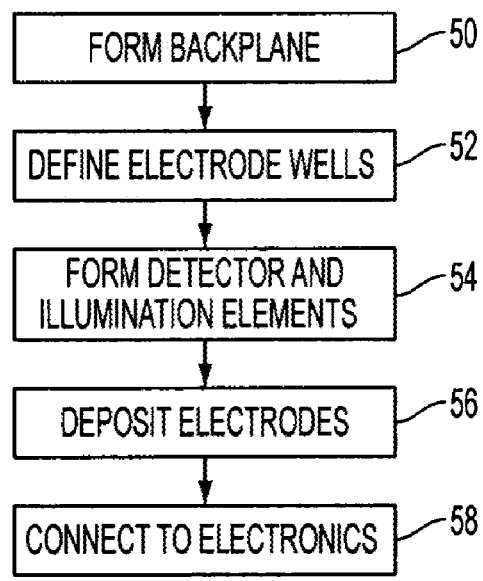
FIG. 6 shows a flowchart of an embodiment of a method of manufacturing a sensor array with integrated illumination.

It is possible to manufacture the hemispherical array in the cut-and-fold method mentioned above and then singularize the detectors and bring them into their spherical shape. The detectors would then just need to be connected to external electronics for readout, driving and power supply. FIG. 6 shows an embodiment of a method of manufacturing a sensor array with integrated illumination.

A modified backplane may be built at 50, containing both readout and driving capabilities. On top of the backplane, an insulating, patterned layer could be formed at 52 to define two sets of wells, corresponding with the electrodes for sensing and driving pixels, respectively. The appropriate organic semiconductors would be ink-jetted into these wells at 54, creating interspersed and individually addressable sets of photodetector elements and illumination pixels. Evaporated electrodes could be used to contact and cover both types of wells at 56, which may or may not be common electrodes for both element groups, depending on the desired between sensor precision and manufacturing ease. If the backplane is at least partially transparent, the covering electrode could be opaque. Otherwise, a translucent or transparent electrode would be needed.

Once the active electronic elements are formed, the flexible substrate would be cut in regions that were predetermined as part of forming the detector array. These predetermined regions would not have any active elements, allowing for the cuts. Once cut, the flexible substrate would be bent into a shape approximating a hemisphere. This would be followed by connection to driving and readout electronics at 58, mentioned above.

For reasons of stray light suppression and sensitivity, it may be advantageous to create a selective optical relationship between the measured spot on the sample and each photodetector element. The optical or micro-optical elements would typically apply net positive optical power to the radiation received from the sample region. The optical elements would typically be situated on top, where the top is the side facing the sample region of the respective pixels on the hemispherical array, and can take the form of arrayed refractive microlenses, diffractive optical elements, reflective optical elements or some combination thereof.

For some embodiments that comprise a transparent backplane stack, even arrayed reflective optical elements could be used with some stray light benefits. Reflective elements would typically be situated below (meaning on the side opposite to the sample region) of the respective pixels on the hemispherical array. In addition, optical elements may be used beneficially in the illumination pathway. This will shape the typically wide emission profile of the sources, such as the roughly lambertian-type profile of an OLED pixel, which would otherwise flood the inside of the hemisphere with excessive background light levels. The optical elements may take the form of simple collimating microlenses to direct that light to the measurement spot. However all optical realizations mentioned above, or known to those skilled in the art could be applied as well. It should be noted, that the optical elements described so far would not have to meet the more stringent optical quality requirements typically imposed on "imaging optics", but rather act as a "non-imaging" or illumination optical element for the pixel(s) each of them serves.

Including arrayed optical elements would also allow additional access to some degree of spatial resolution. In addition to using one microlens per illumination element, one could use one microlens element per several photodetector elements. All of the elements in this group detect light that is emitted into approximately the same solid angle subtended by the lens's aperture. Each of the sub-elements of the group is approximately optically conjugated to a slightly different location in the vicinity of the measurement spot. This could provide useful clues about the subsurface scattering that is happening in the volume under the measurement spot.

Another aspect of the system lies in the polarization dependence of the BRDF measurement. Polarization can be used differentiate between specularly reflected light only on the surface, and scattered light on or under the surface. This has particular value in the context of human skin and diagnostics. This may involve dividing the detector elements into 2 subsets, being responsive to mutually orthogonal polarization types. This may furthermore involve dividing the source elements into 2 subsets, emitting mutually orthogonal polarization types. The polarization selectivity in both cases may be achieved in several ways known to the art. As a proof of existence, the example of patternable polarizing elements available from the company Codixx (Barleben, GER) is referenced here.

In this manner, a compact BRDF measurement system may be implemented. The BRDF measurement system has multiple detectors in a hemispherical array that allows simultaneous measurement of several angles of reflection for a particular angle of incidence, making the system potentially faster, potentially mass manufacturable, and more widely applicable than currently available systems.

It will be appreciated that several of the above-disclosed and other features and functions, or alternatives thereof, may be desirably combined into many other different systems or applications. Also that various presently unforeseen or unanticipated alternatives, modifications, variations, or improvements therein may be subsequently made by those skilled in the art which are also intended to be encompassed by the following claims.

What is claimed is:

1. A measurement system, comprising:
   a non-flat detector array having multiple detector elements arranged on a flexible substrate, the detectors fabricated from a thin film semiconductor comprising one of either amorphous silicon or an organic material ink jet printed into wells on the substrate, the detectors each having baffle structures;
   one or more illumination sources arranged to provide more than one angle of incidence of light on a subject being measured; and
   a detection system in electrical communication with the detector array, the detection system arranged to receive inputs from the detector array and provide a measurement from the inputs.

2. The measurement system of claim 1, wherein the non-flat detector array has the multiple detectors arranged such that the detectors operate simultaneously.

3. The measurement system of claim 1, wherein the non-flat detector array further comprises optical elements arranged adjacent the detector elements.

4. The measurement system of claim 1, wherein the illumination source is external to the detector and the detector has an opening to admit light from the illumination source.

5. The measurement system of claim 1, wherein the illumination source comprises at least one illumination element integrated into the detector array.

6. The measurement system of claim 5, further comprising an optical element arranged adjacent the illumination element such that light from the illumination element is directed to a measurement spot.

7. The measurement system of claim 5, wherein the illumination element comprises one of a light emitting diode, an organic light emitting diode, a laser, or a laser diode.

8. The measurement system of claim 1, wherein the detection system also includes drive electronics to drive illumination elements arranged in the detector array.

9. The measurement system of claim 1, further comprising an absorptive plate having an aperture arranged between the detector array and material under inspection.

10. The measurement system of claim 1, wherein the non-flat detector is arranged on a flexible substrate such that elements of the detector array have locations that are closer to a sphere centered on a sample region than to any selected plane.

11. The measurement system of claim 1, further comprising polarization filters arranged adjacent the detector array.

12. The measurement system of claim 11, wherein the polarizing filters comprise patterned polarization filters.

13. A method of manufacturing a detector array, comprising:
  forming a back plane on a flexible substrate, the substrate having regions in which no active elements are formed the cutting of which would otherwise interfere with operation of the backplane if active elements were present;
  patterning an insulating layer on the back plane to define two sets of wells;
  depositing material by ink-jet printing into the two sets of wells such that one set of wells receives material for photodetection and one set of wells receives material for illumination;
  forming a contact electrode over the wells, resulting in the formation of photodetectors and illumination elements;
  cutting the substrate in the regions in which no active elements are formed; and
  bending the substrate to form an approximation of a hemisphere.

14. The method of claim 13, wherein depositing the material comprises depositing organic materials for organic light emitting diodes and organic photodiodes.

15. The method of claim 13, further comprising connecting the detector array to readout and drive electronics.

* * * * *